US009696270B1

(12) United States Patent
Roy et al.

(10) Patent No.: US 9,696,270 B1
(45) Date of Patent: Jul. 4, 2017

(54) THERMAL CONDUCTIVITY MEASUREMENT APPARATUS AND RELATED METHODS

(71) Applicant: The United States of America as represented by the Secretary of the Air Force, Washington, DC (US)

(72) Inventors: Ajit K Roy, Beavercreek, OH (US); Robert Wheeler, IV, Hilliard, OH (US); Sabyashachi Ganguli, Beavercreek, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 472 days.

(21) Appl. No.: 14/299,021

(22) Filed: Jun. 9, 2014

(51) Int. Cl.
  *G01N 25/18* (2006.01)
  *G01K 7/18* (2006.01)

(52) U.S. Cl.
  CPC ............ *G01N 25/18* (2013.01); *G01K 7/186* (2013.01)

(58) Field of Classification Search
  CPC ...................................... G01N 25/18
  USPC ........................................... 374/44
  See application file for complete search history.

(56) References Cited

U.S. PATENT DOCUMENTS 8,220,989 B1 * 7/2012 Miller .................... G01N 25/18
  374/43
9,170,223 B2 * 10/2015 Hyun ..................... G01N 25/18

OTHER PUBLICATIONS

Shi (Mesoscopic Thermophysical Measurements of Microstructures and Carbon nanotubes, dissertation dated Spring 2001, Chapter 5, pp. 96-119).*

(Continued)

*Primary Examiner* — Clayton E Laballe
*Assistant Examiner* — Leon W Rhodes, Jr.
(74) *Attorney, Agent, or Firm* — AFMCLO/JAZ; Jason Sopko (57) ABSTRACT

An apparatus for thermal conductance measurement includes a first heater assembly having a beam, a platen disposed at an end of the beam, and a heating element and a Resistance Temperature Device (RDT) disposed on the platen. The embodiment further includes a second heater assembly having a second beam, a second platen disposed at an end of the second beam, and a second heating element and a second Resistance Temperature Device (RDT) disposed on the platen. A test rig is also included, and the first heater and second heater assembly are mated to the test rig and separated by a gap length.

8 Claims, 10 Drawing Sheets

(56) References Cited

OTHER PUBLICATIONS

Canetta et al ("Measuring thermal conductivity of polystyrene nanowires using the dual-cantilever technique", Rev. Sci. Instrum. 85, 104901 (2014)).*

Pope et al (Apparatus for the rapid measurement of electrical transport properties for both "needle-like" and bulk materials, Review of Scientific Instruments 72, 3129 (2001); doi: 10.1063/1.1380390).*

P. Kim, L. Shi, A. Majumdar, and P.L. Mceuen, Thermal Transport Measurements of Individual Multiwalled Nanotubes, Phys. Rev. Lett. 87, 215502 (2001).

S. Ganguli, R. Wheeler, S. Sihn, P. Shade, and A.K. Roy, Thermal conductivity measurement at micrometer length scales based on a temperature-balance method, Measurement Science and Technology, Meas. Sci. Technol. 24 (Jun. 2013) 075006 (13pp).

Ajit K. Vallabhaneni, Bo Qiu, Jiuning Hu, Yong P. Chen, and Ajit K. Roy et al, Interfacial thermal conductance limit and thermal rectification across vertical carbon nanotube/graphene nanoribbon-silicon interfaces, J. Appl. Phys. 113, 064311 (Feb 2013).

* cited by examiner

THERMAL CONDUCTIVITY MEASUREMENT APPARATUS AND RELATED METHODS

RIGHTS OF THE GOVERNMENT

The invention described herein may be manufactured and used by or for the Government of the United States for all governmental purposes without the payment of any royalty.

FIELD OF THE INVENTION

The present invention relates generally to methods and apparatus for performing thermal conductivity measurements, and more particularly to performing such measurements on ultra-small test specimens.

BACKGROUND OF THE INVENTION

Current thermophysical measurement techniques experience difficulty in acquiring transport properties along the length of very small specimen (such as, by way of example, carbon nanotube "yarns"). Such materials have lateral dimensions of tens or hundreds of microns and exhibits substantially different thermal conduction in their axial and transverse orientations due its inherent directional lattice morphology. Modeling the bulk properties of composites containing micro-scale or nano-scale fibers or particulates requires knowledge of the properties of the individual constituents, because the nanoscale/microscale thermophysical properties of materials are markedly different from their macroscale properties.

Many other materials, such as nonmetallic fibers or nanotube forests grown on 2 dimensional surface, exhibit strong anisotropic thermal behavior due to structural characteristics. Some materials possess multiphase mixtures and will have very different thermal properties at the microscopic dimension of the phases and at the boundaries between these phases. Still other cases exist where the crystal structure itself is highly anisotropic, leading to quite disparate thermal transport such as that found in layered materials like graphite or perovskite ceramics. In fact, many new materials are designed and fabricated at the microscopic level and below, and do not have macroscopic bodies that can be tested with conventional thermal measurement apparatus.

In each of the cases noted above, traditional methods of measuring thermal conduction through a bulk material cannot be made, and they do not accurately reflect the thermophysical properties of the microscopic or nanoscopic constituents of a material or structure.

Though there is an abundance of theoretical studies on thermal transport properties of micro- and nano-structured materials, experimental measurement at these length scales are still challenging and thus scarce. Conventional thermal measurement techniques with devices at the micro- and nano-meter length scales do not have sufficient spatial resolution to determine accurate temperature and resulting thermal conductivity. Recently, several microscale temperature measurement techniques have been investigated by different groups using 1) far-field optical techniques, such as infrared emission, laser surface reflectance, and liquid crystal microscopy, 2) near-field optical thermometry techniques, and 3) non-optical techniques, such as scanning thermal microscopy (SThM) and a photo acoustic technique.

The spatial resolution of the far-field optical techniques is limited by optical diffraction wavelength to the order of approximately 1 μm or larger. With the near-field optical techniques, the spot size could be reduced to a fraction of the wavelength by using a solid immersion lens. Near-field thermometry has reportedly enabled sub-micrometer spatial resolution, and SThM is capable of thermally resolving sub-100 nm features with a proper design of SThM probes. While the noted conductivity measurement methods have their own merits, these indirect measurement techniques tend to yield qualitative rather than quantitative data and often rely on modeled localized thermal flow.

Another measurement technique applied to the microscale specimens is thermal conductance evaluation. Among different thermal conductance schemes, a 3ω method is the preferred choice for the in-plane thermal conductivity measurement of thin films. However, the 3ω method does not produce acceptable results for the thermal property measurements of freestanding microscale structures such as fibers.

One possible apparatus for measuring freestanding microscale structures includes a suspended micro-device for measuring the thermal conductivity of silicon nanowires of different diameters (ranging from 22 nm to 115 nm) over a temperature range from 20K to 320K. The apparatus includes two silicon nitride (SiN) membranes suspended by five SiN beams. A thin Pt resistance coil and a separate Pt electrode are patterned onto each membrane. Each Pt resistor serves as a heater to raise the temperature of the suspended elements and also as a resistance thermometer to measure the temperature of each element. Si nanowires are then drop-cast using propanol dispersion to bridge the gap between the two SiN membranes. The entire test procedure may be performed under vacuum inside a Scanning Electron Microscope (SEM), and thermal conductance may be ascertained. Unfortunately, prior systems are only amenable to randomly oriented nanofibers that can be transported to the fixed gap between these heaters and there is no independent control of test temperature and heat flux. Therefore, the test temperature and heat flux through the specimen are dependent on the resistive heating of the Pt elements. Due to this, to maintain a fixed temperature during testing active cooling may be required in prior art configurations.

Therefore, there exists a need for improved methods and apparatus for performing thermal conductance measurements on a wide variety of ultra small specimens.

SUMMARY OF THE INVENTION

The present invention overcomes the foregoing problems and other shortcomings, drawbacks, and challenges of performing thermal conductivity measurements on micro and nano-scale test specimens. While the invention will be described in connection with certain embodiments, it will be understood that the invention is not limited to these embodiments. To the contrary, this invention includes all alternatives, modifications, and equivalents as may be included within the spirit and scope of the present invention.

According to one embodiment of the present invention, an apparatus for thermal conductance measurement is provided. The apparatus includes a first heater assembly having a beam, a platen disposed at an end of the beam, and a heating element and a Resistance Temperature Device (RDT) disposed on the platen. The embodiment further includes a second heater assembly having a second beam, a second platen disposed at an end of the second beam, and a second heating element and a second Resistance Temperature Device (RDT) disposed on the platen. A test rig is also included, and the first heater and second heater assembly are mated to the test rig and separated by a gap length.

According to another embodiment of the disclosed invention, a heater assembly is provided. The heater assembly includes a substrate and a beam extending from a portion of the substrate. A platen is disposed at an end of the beam, and a heating element and a Resistance Temperature Device (RTD) disposed on the platen. Pads form a plurality of conductive regions on the substrate, and a plurality of conducting wires electrically mate the pads to the RTD and to the heating element.

According to yet another embodiment of the disclosed invention, a method for testing the thermal conductance of a specimen in a system having a first platen and a second platen, wherein the first platen includes a first heating element and a first Resistance Temperature Device (RTD), and wherein the second platen includes a second heating element and a second Resistance Temperature Device (RTD). The method includes evacuating the air proximate the first heating element and the second heating element. The method also includes using the first and second RTD to obtain temperature data. A first and second power level is applied to maintain a desired first and second baseline set temperature in each of the first heating element and the second heating element, respectively, while no sample is in place. The first and second power level required to maintain the desired first and second baseline set temperature in each of the first heating element and the second heating element, respectively, is recorded. The method also includes placing the specimen across a gap separating the first platen and the second platen and establishing thermal contact between the specimen and each of the first platen and the second platen. A third and fourth power level is applied to maintain the desired first and second baseline set temperature in each of the first heating element and the second heating element, respectively, while the specimen is spanning the gap between the first platen and the second platen. The method also includes recording a difference in the third and fourth power level required to maintain the first and second baseline set temperatures.

Additional objects, advantages, and novel features of the invention will be set forth in part in the description which follows, and in part will become apparent to those skilled in the art upon examination of the following or may be leaned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

The discussion that follows is directed to a thermal property measurement apparatus and related methods for micro-scaled and nano-scaled structures. Furthermore, the disclosed invention enables thermal testing of specimens under no load, static load, and dynamic loading conditions. In one embodiment of the disclosed invention, two independently controlled micro-heaters are employed. Additionally, according to an embodiment of the inventive methodology, a first heater and second heater are held at a first desired temperature and a second desired temperature, respectively, above the ambient temperature. Then, a first power driving the first heater and a second power driving the second heater are allowed to automatically adjust, via computer control, so as to maintain the first desired temperature and the second desired temperature while a test specimen bridges the gap between the first heater and the second heater. This enables thermal measurements to be made in micron-sized samples over a large temperature range above ambient temperature without necessitating active cooling within the confines of the SEM.

The inventive apparatus enables one to measure the thermal conductivity under various static and dynamic loading conditions. In one embodiment, a silicon micro-electro-mechanical system (MEMS) approach is used to fabricate a dual heater assembly configuration where each heater is suspended at the end of a long self-supported beam. Temperature adjustment in each heater platen may be accomplished by Joule heating of Platinum (Pt) circuits patterned on the surface of the suspended beam heater assemblies. Some embodiments of the disclosed invention further utilize embedded Pt resistance temperature devices (RTDs) for temperature measurement. The temperature measurement using these RTDs embedded within the heater assembly may be calibrated by monitoring the melting point of microsized metal particles as the power is increased.

Figure 1:
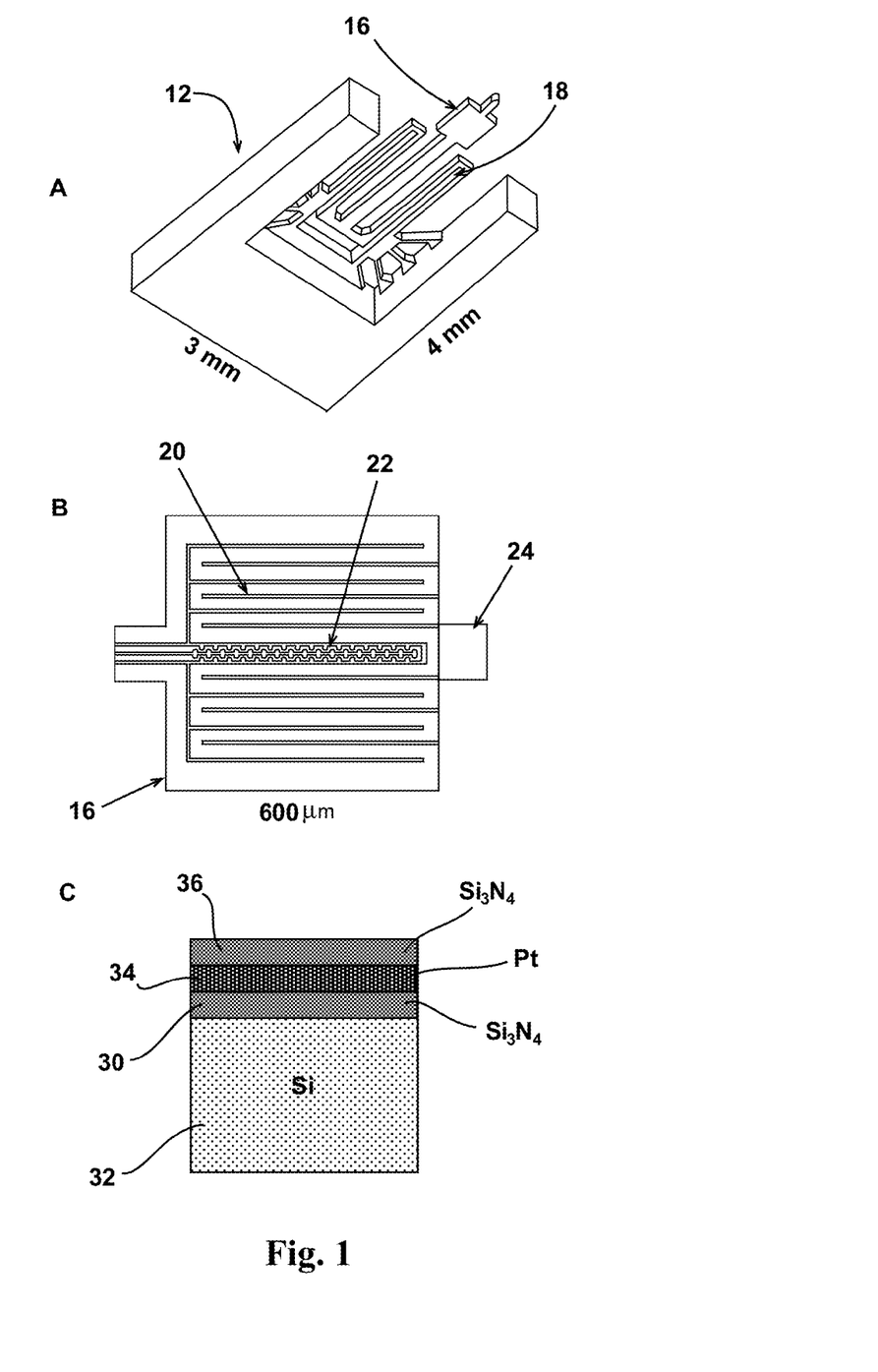
FIG. 1A-1C illustrates various views of a heater apparatus in accordance with embodiments of the disclosed invention.

Turning attention to FIGS. 1A-1C a schematic illustration of a heater assembly 12 is shown in various degrees of detail. It should be noted that while various dimensions and material identifiers have been appended to the figures, they are merely for illustrative purposes. The scale and proportions of various embodiments of the disclosed invention may be varied to achieve design and performance objectives. As seen in FIG. 1A, the heater assembly 12 includes a platen 16 supported by a narrow beam 18 formed of silicon. The beam is generally a skeletonized feature that results from removing substantial adjacent material yet maintaining sufficient robustness to support the platen and specimens under test. Furthermore, the skeletonized feature minimized thermal conductance between the platen and the remainder of the heater assembly 12, by providing a slender circuitous route therebetween. Active heating is accomplished by the platen 16, and the platen 16 is physically supported with respect to the heater assembly 12 by the beam 18. Additionally, the beams 18 also provides a continuous path for electrical conducting leads, thus interconnecting conductors external to the heater assembly 12 to the platen 16.

FIG. 1B shows an enlarged view of the platen 16 of the heater assembly 12. The Pt circuits on the platen 16 of the heater assembly 12 may comprise a serpentine heating element 20 and an RTD 22. For larger micron-sized specimens, a significant length of the sample may be placed in contact with the platen 16 and the serpentine heating element 20. Smaller micro- and nano-scale specimens can be positioned in contact with a small silicon tip 24 disposed adjacent the heating element 20. In order to establish good thermal contact between the heater assembly 12 devices and specimen, thermal grease can be employed.

The heater assembly 12, as shown in FIGS. 1A-1B, may be fabricated in accordance with the layered structure as shown in FIG. 1C. In one embodiment, the heater assembly 12 may be created by depositing an insulating dielectric layer 30, for example silicon nitride ($Si_3N_4$), on a substrate 32 (for example, Si). A standard photolithography technique may be used to pattern a metal layer 34 (by way of example, Pt) for the heating element 20 and the RTDs 22 on the substrate 32. In order to reduce the thermal mass of the heater assembly 12, the starting thickness of the substrate 32 may be locally thinned from the backside by deep reactive-ion-etching (DRIE). This may yield platen 16 having a final thickness of approximately 70 μm. Subsequently, the platen 16 and beams 18 may be isolated from the bulk contact pads (shown in FIG. 2) by creating trenches in the front side of the substrate 32 by the DRIE. Finally, another layer of silicon nitride can be deposited as an insulating capping layer 36 on the device, as shown in FIG. 1c.

Figure 2:
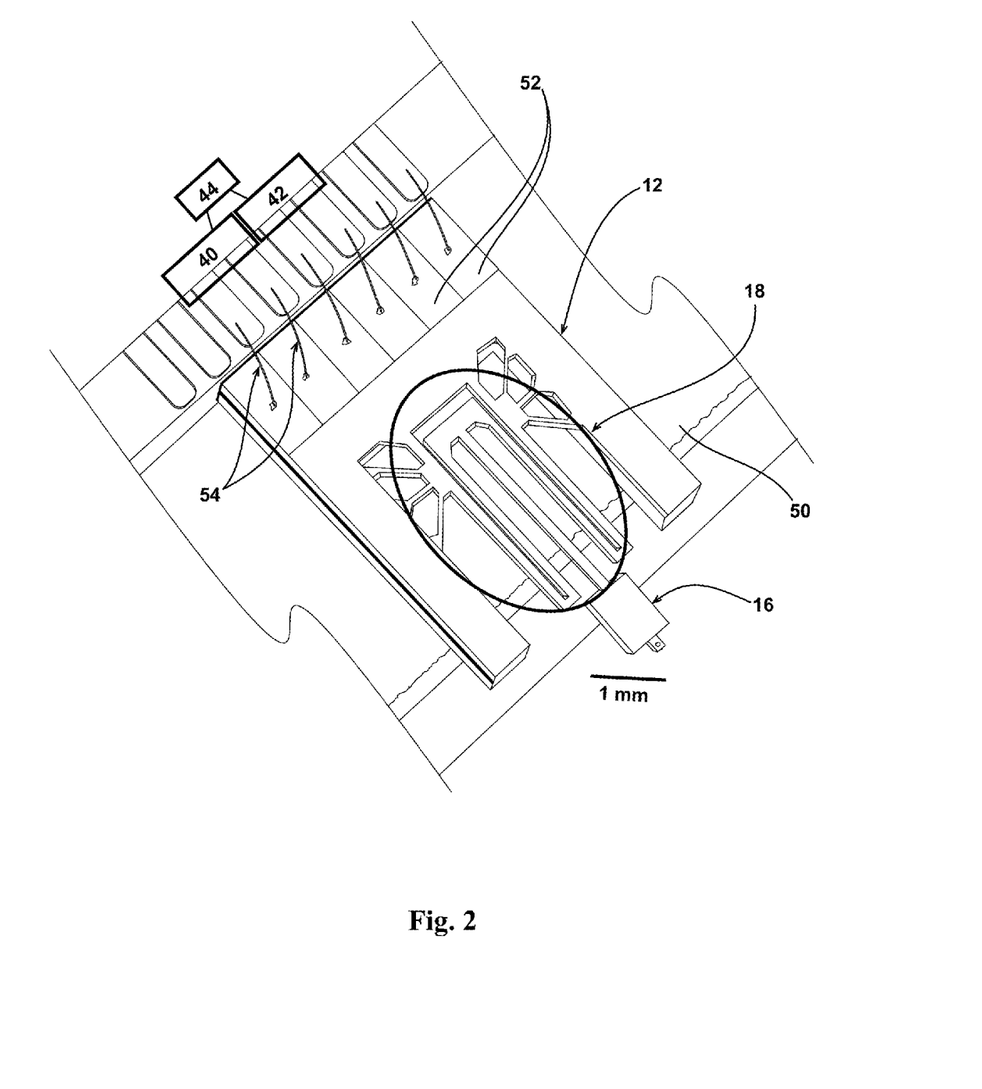
FIG. 2. Illustrates a detailed view of a heater apparatus mated to a Dual Inline Package.

Two of the heating assemblies 12, as shown in FIG. 2, are necessary to perform a thermal conductivity measurement in accordance with the disclosed invention. Each of the first heater assembly 12a and second heater assembly 12b (shown in FIGS. 3 and 8) may be powered by a high sensitivity DC power supply 40. Resistances in the RTD 22 must be monitored using a high-precision source measuring unit (SMU) 42 or digital multi-meter (DMM). A controller 44 is used to monitor the two SMU 42 resistance values corresponding to the first heater assembly 12a and the second heater assembly 12b, respectively, in a dynamic feedback loop to continually adjust the power levels supplied to the heater assemblies 12a and 12b. In this manner, each of the heater assemblies 12a and 12b is maintained at its respective desired temperature. Typical thermal conductivity tests may be performed near room temperature with nominal temperature difference of approximately 10° C. between first heater assembly 12a and the second heater assembly 12b. While many of the examples disclosed herein focus on a temperature difference or differential of 10° C., difference of 2 to 100° C. may produce acceptable results.

In one exemplary set of heater assembly 12 devices comprising a first heater assembly 12a and a second heater assembly 12b, the room temperature resistances in the heating elements 20 and the RTDs 22 measured approximately 400Ω and 950Ω, respectively. Smaller test specimens are typically placed across the gap between two platens 16 or two tips 24 using a nanomanipulator. Both calibration and actual measurement of the thermal conductivity are performed inside the SEM having a chamber pressure of approximately 13.3 μPa (1e torr), however pressures between $10^{-7}$ and $10^{-3}$ torr have been shown to produce acceptable results. The first heater assembly 12a and second heater assembly 12b may be mounted in a conventional ceramic dual in-line package (DIP) 50 for electrical wiring, as shown in FIG. 2. Pads 52 are interconnected to the DIP 50 by wires 54.

The disclosed method for microscale thermal conductivity measurement resolves many of the deficiencies found in the prior art. For example, in ambient environments, accurate measurements can be challenging because of contributions of all three heat transfer modes; radiation, convection and conduction. However, the disclosed method is carried out at relatively low temperatures (approximately 70° C. for the first heater assembly 12a and approximately 60° C. for the second heater assembly 12b) to minimize radiation losses. Additionally, the disclosed apparatus is placed in the vacuum chamber of the SEM to minimize the convection contributions to the measurements.

In some prior art measuring techniques, the measured specimen is positioned between two reference heaters held at two different temperatures using thermal grease to reduce the interfacial thermal contact resistance between the specimen and heater. Numerous RTDs 22 are placed along the length of a test specimen. These yield information on the rate of heat flow (heat flux) through the specimen. The heat flux can then be used to determine the thermal conductivity of the unknown specimen using a one-dimensional Fourier's conduction equation:

$$q = -\kappa(\Delta T/\Delta x) \quad \text{Equation 1}$$

Where q is the normalized heat flux, κ the thermal conductivity, and (ΔT/Δx) the temperature gradient with respect to the heat flow direction (x-direction in this case). Here, the temperature difference between RTDs 22 is given by ΔT and the distance over which the temperature difference is measured is given by Δx.

During testing with the apparatus described in the present invention, two different levels of DC electric power are supplied to the two nominally identical heater assemblies 12. Joule heating results from the electric current in the device's serpentine platinum heating element 20. The Joule heating then increases the temperatures of each of the first heater assembly 12a and the second heater assembly 12b to a desired temperature above the ambient temperature, denoted by $T_H$ and $T_C$ for their relative first and second temperatures, respectively. When measuring the thermal conductivity, the heat flux in Eq. 1 is determined using the DC power values in each platen 16 while the temperatures are maintained at their predefined set values, first without a specimen bridge in place and then with the specimen bridging the gap between the heater assemblies 12a and 12b. Prior to bridging the gap with a test specimen, the temperatures of each heater assembly 12a and 12b is raised to their desired values, $T_H$ and $T_C$. The controller 44 regulates and monitors the power supplies 40 and SMUs 42. The controller 44 monitors the RTDs 22 and directs power adjustments to each heater assembly 12a and 12b in order to maintain the desired set temperatures. Once a steady-state heating condition is established for each platen 16 (i.e. no change in the power level with time), the baseline power values, $P_H$ and $P_C$, are recorded. These are associated with the higher and lower Joule heating requirements to maintain the two discrete heater assembly 12a and 12b temperatures. Thus, the baseline power values are determined to maintain the $\Delta T = T_H - T_C$ value for the open thermal circuit (i.e. no specimen).

Figure 3:
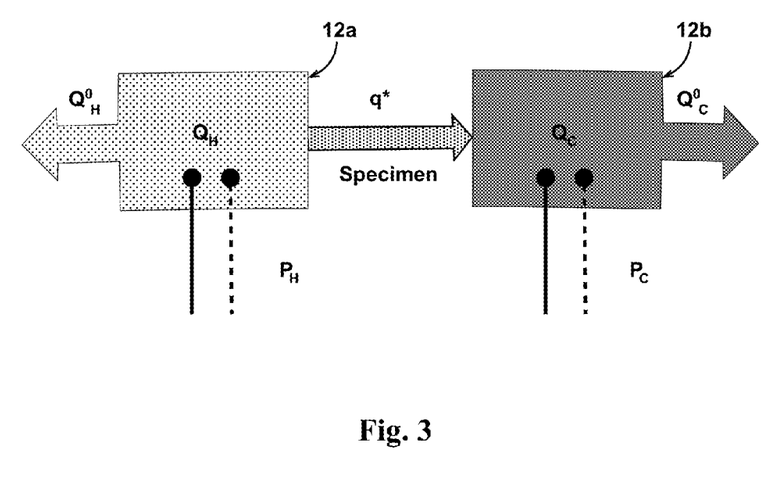
FIG. 3 is a schematic representation of thermal flow of a first and second heater apparatus according to an embodiment of the disclosed invention.

Once a specimen is placed on the platens 16, thermally connecting them as shown schematically in FIG. 3, new power settings are required for the closed thermal circuit to maintain the same desired temperature values for the heater assemblies 12. The DC power supplied to the first heater assembly 12a in the closed circuit must be increased by $\Delta P_H$ relative to the open circuit configuration, so that $P_H' = P_H + \Delta P_H$. Here, the prime is used to denote the closed thermal circuit configuration. Neglecting the convective and radiant heat losses, the excess induced Joule heating, reflected in $\Delta P_H$ required by the first heater assembly 12a is associated with the heat flux through the specimen bridge to the second heater assembly 12b. In order to maintain the desired set temperatures at both heater assemblies 12a and 12b, and thus the temperature difference, $\Delta T$, the transferred heat must also be compensated at the second heater assembly 12b by lowering the DC power by $\Delta P_C$, so that $P_C' = P_C + \Delta P_C$. Neglecting interfacial effects, the changes in power from open to closed circuit conditions yield the total amount of the heat flux, q*, from the following relations:

$$P_H - P_C = (P_H + \Delta P_H) - (P_C + \Delta P_C) = (P_H + q^*) - (P_C + q^*) \quad \text{Equation 2}$$

which leads to $$q^* = (\Delta P_H + \Delta P_C)/2. \quad \text{Equation 3}$$

After measuring the cross-sectional area A of the specimen, we finally calculate the heat flux, q, as follows:

$$q = q^*/A \quad \text{Equation 4}$$

Finally, thermal conductivity is computed as $$k = -q(\Delta x/\Delta T) \quad \text{Equation 5}$$

Note that the power variation in each heater assembly 12 should be equal in magnitude but opposite in sign. Since the platens 16 are held at constant temperature under both open and bridged conditions, both the heating element 20 and electrical lead resistance values remain constant during testing. Thus, a schematic of the relent thermal characteristics is illustrated in FIG. 3.

An embedded platinum RTD 22 was calibrated according to a modified International Temperature Scale 1990 (ITS-90) standard. In the full ITS-90 system, the calibration would be performed throughout a temperature range from −259.35° C. to 961.75° C. However, in the current study, the RTD 22 was calibrated within a limited range from room temperature to about 328° C. During this fixed point calibration, the electrical resistance within the integrated RTD 22 circuit was monitored while the temperature of the platen 16 of the heater assembly 12 was raised at a constant rate to three accurately known conditions. These three unique conditions represent known temperatures associated with the solid to liquid transformation during melting of three elemental metal microspheres. These microsized calibration specimens 59 (microspheres) were placed on the platen 16 of a representative standard heater assembly 12 and were chosen for their low melting points. These metals; Indium, Tin and Lead, have melting temperatures of 156.6° C., 231.9° C. and 327.5° C., respectively. The specific heater power conditions for melting were determined by making in-situ observations of the physical changes associated with melting of the metal micro particles within the SEM.

Figure 4:
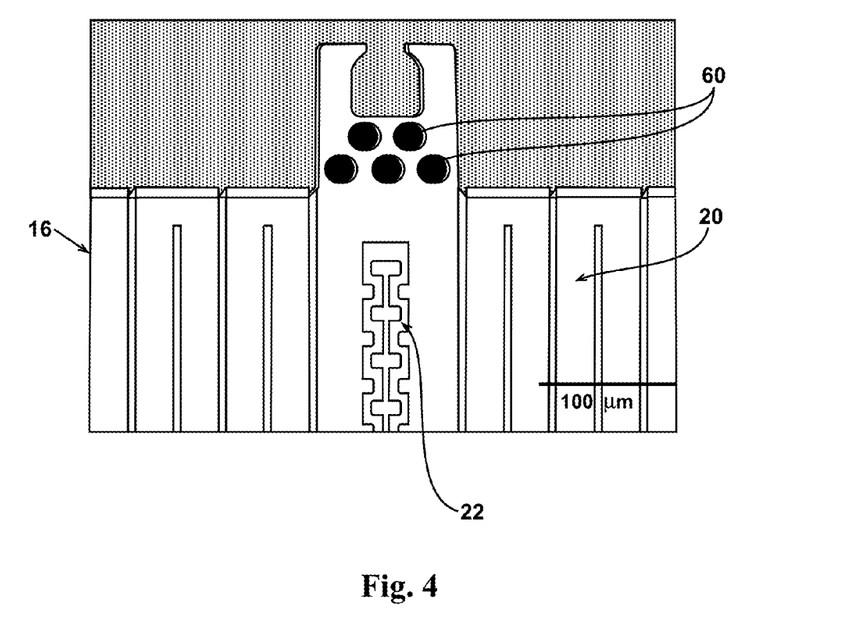
FIG. 4 is a top view of a heater assembly highlighting a heating element, resistance temperature devices, and receptacles.

This temperature calibration was performed in the SEM under high vacuum conditions of $10^{-7}$ torr. Initially, the actual room temperature value of the heater assembly 12 was measured with a thermocouple placed on the stage of the SEM prior to heating the heater assembly 12. Then, the melting temperature of each calibration specimen 59 was determined by raising the temperature of the heater assembly 12 platen 16 and observing the sequential melting events via live electron imaging. Each of these metals undergoes a volume expansion during the solid to liquid transformation and so can provide visual evidence of the phase change. To facilitate this calibration, a dual-beam focused ion beam (FIB) was used to micro-machine small receptacles 60, with a diameter of approximately 20 μm, into the surface of the heater assembly 12 near the sample mounting area and adjacent to the heating element 20 and the RTD 22, as shown in FIG. 4. For each metal, finely sieved elemental powders, with purities greater than 99.99% by weight, were procured for placement into the receptacles 60. Positioning of individual particles into the FIB machined receptacles 60 was carried out using the micromanipulator system of the FIB while imaging with the electron beam. Spherical components of Indium and Lead, with diameters somewhat less than 20 μm, were located for placement into the retaining cups. However, the supply of Tin powders did not present such uniform shapes and so an elongated, larger particle was selected for the melting point temperature calibration.

Figure 5:
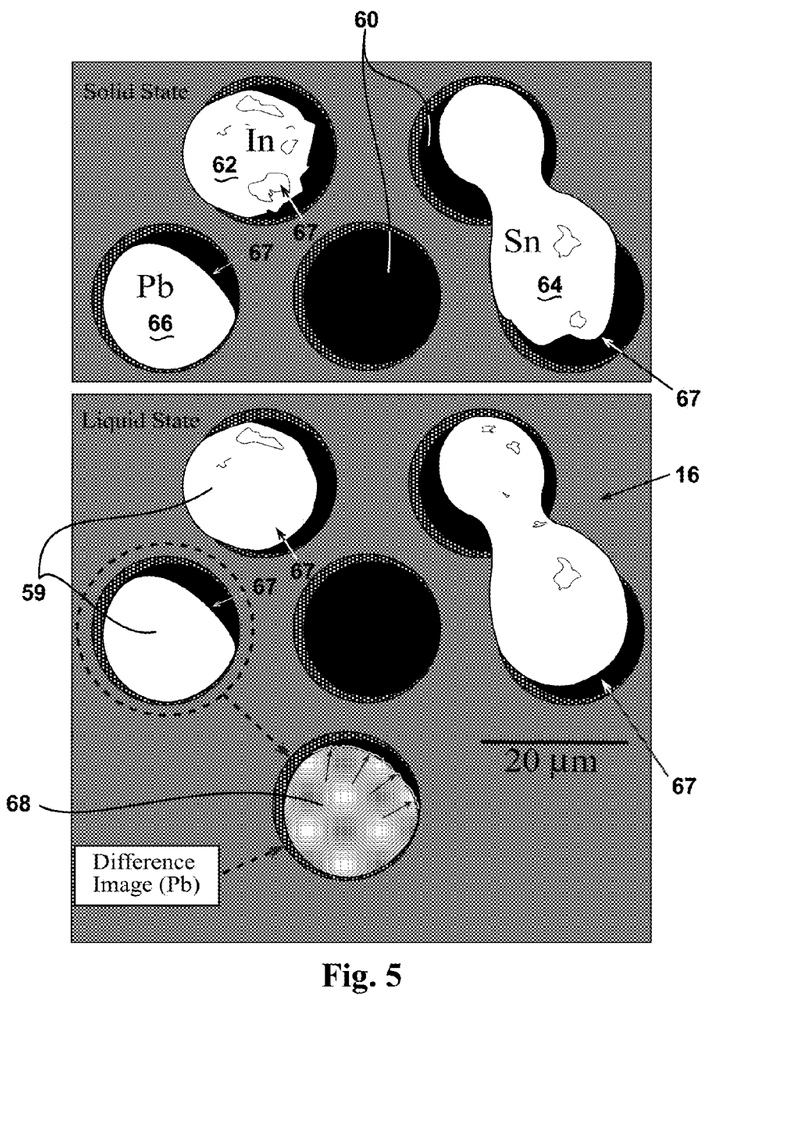
FIG. 5 illustrates a plurality of calibration specimens and related phase change indicators.

FIG. 5 shows the three metal micro specimens 59 after placement into selected receptacles 60 on the heater assembly 12 platen 16. During calibration of the embedded RTD, the heating element 20 power was gradually increased, raising the platen 16 temperature from room temperature to temperatures above the melting points of each micro-particle; In 62, Sn 64, and Pb 66, in succession. This was done while simultaneously monitoring the resistance in the RTD 22 circuit and capturing electron images of the metals. The shapes of metals within the receptacles 60 presented in FIG. 5 are all unique but each gives clear indication of the solid and liquid states. During initial heating above a power level that resulted in the melting of all three metals, the In 62 and Sn 64 particles formed local thermal contact with the walls of the FIB machined receptacles 60 yet retained their general initial shape. On the other hand, the starting Pb microsphere (not shown) wetted the receptacle 60 wall as shown in FIG. 5. On cooling below their melting points, the In 62 and Sn 64 metals show surface morphology in the SEM images that have rough or dimpled surfaces while the Pb 66 droplet retains a shape conforming to the receptacle 60 walls.

Once thermal contact was made between each metal and the receptacle 60, the RTD 22 temperature calibration proceeded by cycling the temperature above and below the critical power levels associated with melting for a particular metal. FIG. 5 shows the unique morphology of each calibration specimen 59 when viewed in their solid and liquid states. Specific phase change indicators 67. As the heater assembly 12 platen 16 temperature was elevated above 156.6° C. (429.7K), the featured dimple on the In 62 sphere rapidly expanded while the interior metal transformed to the liquid state. This is due to the volume expansion associated with the solid to liquid phase change. The general shape retention can be attributed to the presence of an oxide layer on the surface. A similar morphology change was observed in the transformation of the Sn 64 calibration specimen 59. As the temperature was raised above 231.9° C. (505.1° K), the end of the elongated Sn 64 particle expanded as seen in FIG. 5. The Pb 66 micro specimen behaved in a unique manner, showing a uniform expansion of the free surface away from the wall of the receptacle 60. As the temperature was raised above 327.5° C. (600.7K), a small change in sample size was seen. The resulting movement of the entire free surface of the droplet is detected in the difference image 68 that gives the magnitude of the shape change as the output of an optical comparator.

Figure 6:
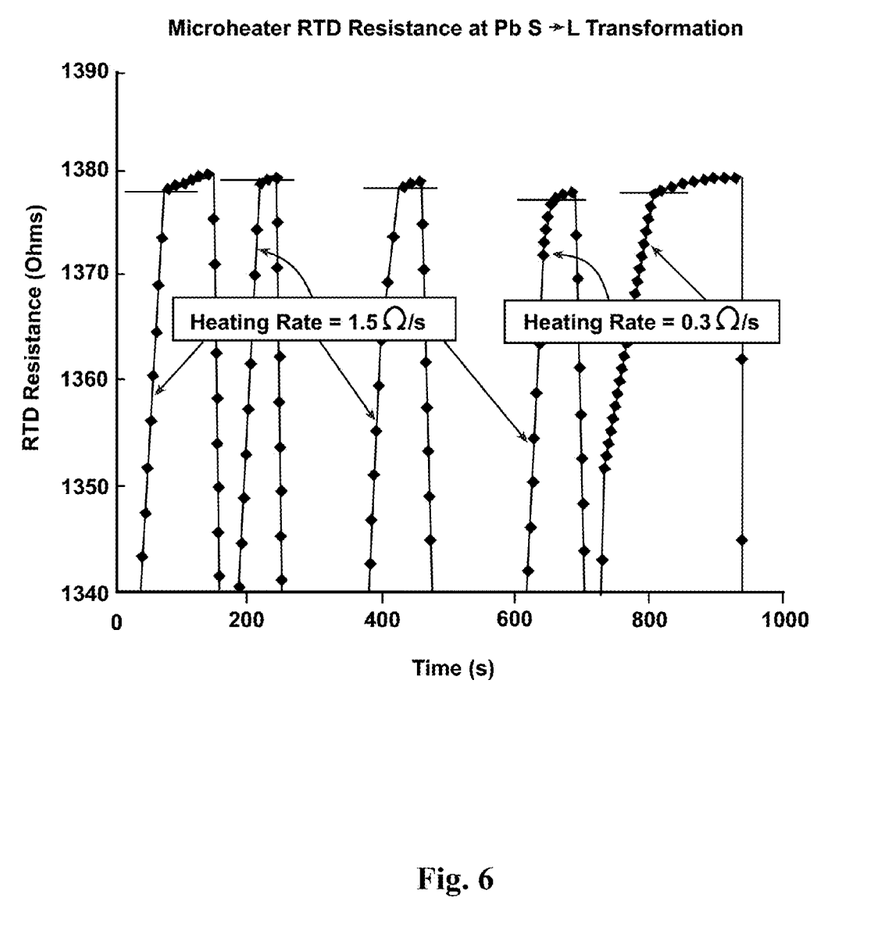
FIG. 6 is a graph of calibration heating curves according to an embodiment of the disclosed invention.

Near each characteristic melting point, the temperature of the heater assembly 12 platen 16 was cycled above and below the melting temperature so that the resistance coinciding with each melting event could be identified. In all tests, different heating ramp rates were considered for temperature change prior to melting. A faster rate of 1.5 Ohms/s and a slower rate of 0.3 Ohm/s were used for these heating ramps. During all the melting events, the RTD 22 resistance was captured by manually halting the heating ramp as soon as the morphology change occurred. Continuous monitoring of resistance values was recorded in a data log file that has been plotted as a function of time in FIG. 6, for the melting of the Pb 66 droplet. Horizontal lines indicate the RTD 22 value recorded at the moment of melting and is taken as the resistance in the RTD 22 circuit corresponding to a heater assembly 12 platen 16 temperature of 600.7K. Then, after several seconds, the power was reduced and the heating assembly 12 cooled, eventually transforming the metal back to the solid state. Five cycles were considered in the determination of the resistance for 600.7K. FIG. 6 shows that the RTD 22 resistance continues to slowly climb as the power to the heater assembly 12 is held constant when melting was detected. This indicates that the entire heater assembly 12 has not come to thermal equilibrium for the ramp rates employed here. The controller 44 will compensate for this drift in temperature during the hold condition of the thermal conductivity measurement.

Figure 7:
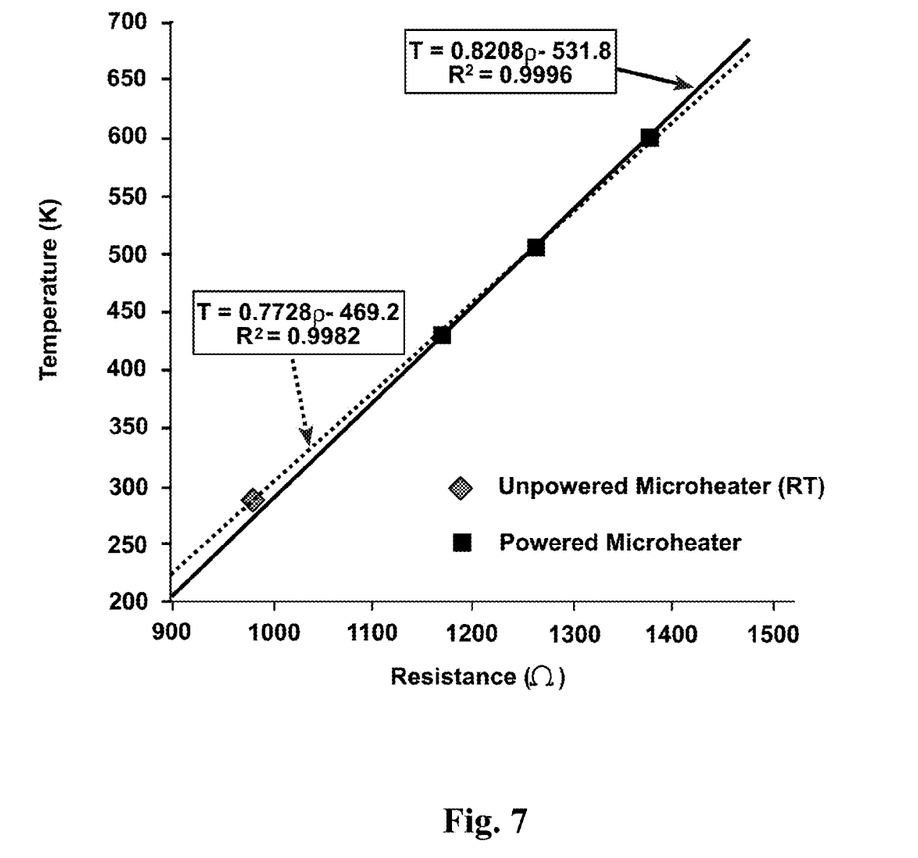
FIG. 7 is a graph showing calibration results according to an embodiment of the disclosed invention.

Temperature calibration of the RTD 22 circuit is accomplished by plotting the resistance values for conditions at the four known heater assembly 12 platen 16 temperatures. FIG. 7 displays the temperature versus RTD 22 resistance calibration curve for the heater assembly 12 in FIG. 4. Two least-squares regression fit trend lines are displayed in the figure, one associated only with the three melting conditions and one including the additional room temperature resistance value. The linear fit of the three melting state data values is highly correlated with a coefficient of determination of 0.9996. However, the room temperature resistance is not predicted accurately from this fit. It was noted above that the powered heater assembly 12 is not in thermal equilibrium during the temperature ramp and hold stage of calibration. This non-equilibrated heater assembly 12 condition will affect the error associated with the accuracy of these temperature measurements. The fit using all the calibration data, including the room temperature value, is not as well correlated as with the three metals alone. Since many applications will employ powered heater assemblies 12 during thermal conductivity measurement, the powered heater assembly 12 linear fit will be used to measure temperature. A second heater assembly 12b (or higher order) can be calibrated using the first heater assembly 12a by bringing a second heater assembly 12b into contact with the first heater assembly 12a while under a powered condition. Power to the second heater assembly 12b is varied such that, upon contact, no change in RTD 22 resistance occurs in the first heater element 12a. At this condition, the temperature of the second heater assembly 12b is known to equal the first heater assembly 12a. Several power conditions may be required to establish the calibration of the second heater assembly 12b.

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Figure 8:
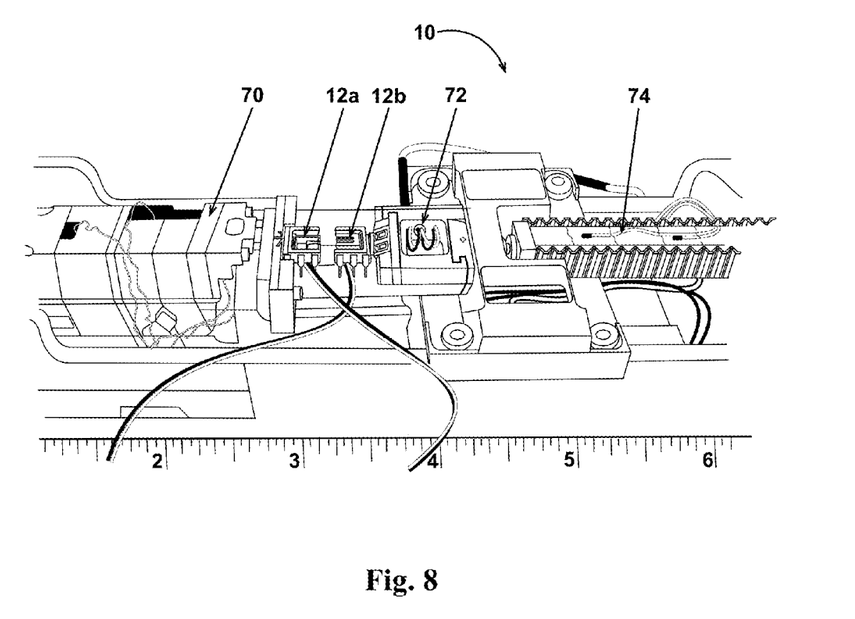
FIG. 8 illustrates a test rig according to an embodiment of the disclosed invention.

Turning attention to FIG. 8, a measurement system 10, includes a test rig 70 having a first heater assembly 12a and a second heater assembly 12b. The test rig 70 may be placed within the evacuated environment of the SEM or FIB. The system 10 is then used to measure the thermal conductivities of several standard metal wires and, thereby, validate the overall calibration and accuracy of the system 10. This system 10 provides the added functionality of applying tensile or compressive loads to the specimens while heating during thermal conductivity measurement. To validate the thermal conductivity methodology, a constant gap between the heater assemblies 12a and 12b of approximately 2 mm is maintained. Specimens are loaded onto the two opposing suspended beam heater assemblies 12 configured in the test rig 70 as shown in FIG. 8 (and the detailed view of FIG. 9). A positioning stage 72 is configured to provide XYZ positioning, and is used to align the heaters 12a and 12b adjust the resulting separation gap. An actuator 74 may apply an axial force to the second heater assembly 12b and connected sample, and a load cell 76 measures the resulting force transferred to the sample.

Figure 9:
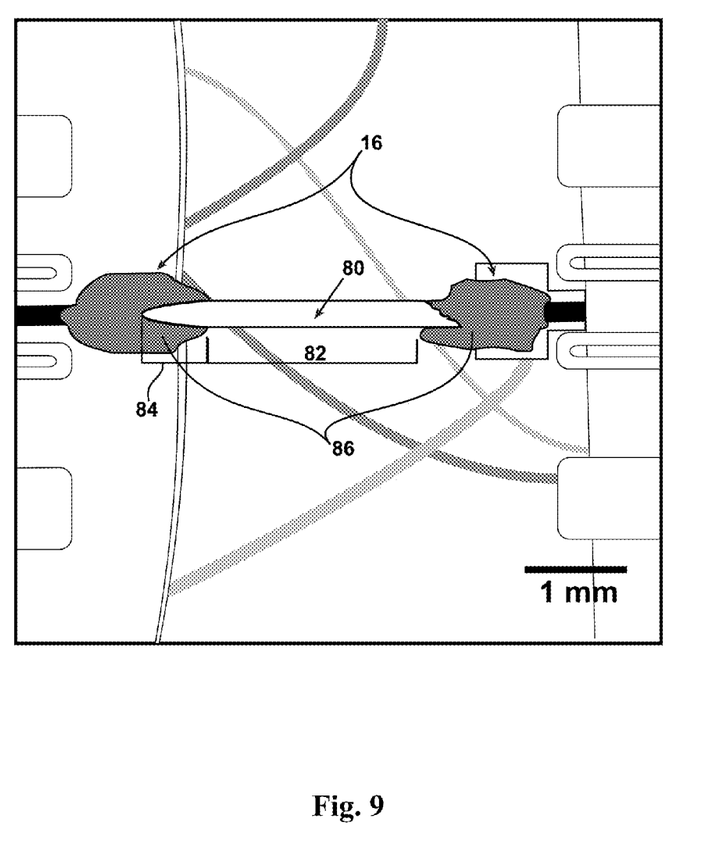
FIG. 9 illustrates a test specimen spanning a first and second heater assembly according to an embodiment of the disclosed invention.

In FIG. 9, the heater assemblies 12a and 12b are shown with a validation specimen 80 bridging the gap length 82 between the heater assemblies 12a and 12b during testing. The platens 16 of the heater assemblies 12a and 12b receive the validation specimen 80 and the thermal interface therebetween may be improved with an application of thermal paste (such as Omegatherm® from Omega Engineering®, or the like).

Wire validation specimens 80 were prepared for measurement by first cutting short lengths with a razor blade on a glass slide. These validation specimens 80 were manually transferred to the platens 16 using a fine tip tungsten micromanipulator needle under an optical microscope (not shown). FIG. 9 illustrates that the length of the validation specimen 80 is longer than the gap length 82 so that a substantial amount of overlap 84 is maintained on the platens 16. In measuring the length for computing thermal conductivity, only the length spanning the distance between heater assemblies 12a and 12b (effectively, the gap length 82) is used. The validation specimen 80 in FIG. 9 has ample thermal paste 86 applied to either end of the approximately 150 μm diameter validation specimen 80 wire. In this particular test, the first heater assembly 12a was held at approximately 46° C. while the second heater assembly 12b was maintained at about 36° C. The measurements of thermal conductivity in the validation specimen 80 employed temperature settings near room temperature. In these measurements, the temperature difference (ΔT) was held between 9 and 10 degrees Celsius. The validation specimen 80 length, measured between heater platens, (Δx), was intended to remain at 2 mm, but from FIG. 9, wetting of the wire with thermal paste 86 was taken into consideration in determining this parameter.

Figure 10:
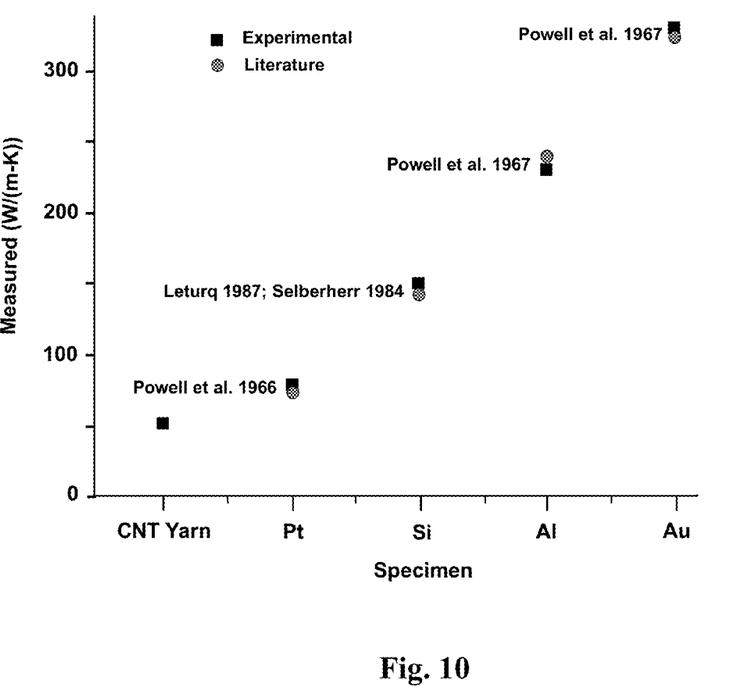
FIG. 10 is a graph comparing experimental thermal conductivity values juxtaposed with literature values.

A series of well-understood metals were selected for testing because of their variability in thermal conductivity. In the temperature balance methodology of the disclosed invention, equation 3 is used to relate the heater assembly 12 power to the heat flow through our validation specimens 80. The power variations required to maintain the set temperatures of our opposing heater assemblies 12 give a quantitative measure of the total heat flux through a given validation specimen 80. The cross-sectional area and length of each validation specimen 80 are used in equations 4 and 1 to yield thermal conductivity values. Data for several metal microwires and the densified nanotube wire are presented in FIG. 10. The measured thermal conductivity of the metals is compared with literature values to validate testing measurement accuracy, and as shown, a high degree of correlation exists for all specimens. This holds true from a poor conductor like Pt to a good conductor as in Au. Also, no clear systematic error can be seen in these data, where three measured thermal conductivities lie above and one below the literature values. This suggests that the contact resistance may not be affected by the native oxides on the validation specimens 80 when using the thermal paste 86. Thus, we see the close agreement with literature values and our measurements for the noble metals, Pt and Au, as well as for metals with more significant surface oxides, Si and Al. The present measurement of the densified nanotube yarn is the first of its kind and appears lower than the values that might be expected for such material. However, considering that no single CNT spans the entire length of the specimen, the densified nanotube wire evidently must have many nanotube-to-nanotube junctions, interacting by weak Vander Waals forces.

In prior art apparatus, a single heating element is energized while the other end of the test specimen is connected to a sensor that reacts to the heat transferred through the test specimen. The sensor temperature changes in response to the power level directed into the heated side. The prior art apparatus and method is in direct contrast to the present invention. In the current invention, both heater assemblies 12 are powered, thus allowing the temperatures of each side to be held constant under either of two operating conditions; either while the heaters are separated (open) or while connected by a test specimen (bridged). The result in the disclosed invention is that all circuit resistances are also held constant, including the lead resistances. Therefore, the electrical power generating energy within each heater assembly 12, causing a net heat flow through a test specimen, is manifested only in the change in current within each heater for the bridged heaters relative to the open heaters. That is, power, given by $P_H = I_H^2 R_H$ and $P_C = I_C^2 R_C$ for the first heater assembly 12a and second heater assembly 12b, respectively, is only a function of the currents, $I_H$ and $I_C$, for both the open and bridged test conditions.

When carried out in a vacuum (or at pressures significantly below atmospheric pressure), the present invention induces one dimensional heat flow within a test specimen under investigation along a direction from the high temperature heat source (the higher heat may be arbitrarily assigned to the first heater assembly 12a or to the second heater assembly 12b) to the low temperature heat sink. A change in electric power is required to maintain both the source and sink heater temperatures unchanged from their open or non-contact condition. This electric power energy, which can be very accurately determined, provides a direct measure of the heat energy flowing through the test sample. Unlike other measurement techniques, active variable power is required to both source and sink heater assemblies while their set temperatures are maintained. Thus, no cooling is required in this new methodology for temperatures above ambient. However, in certain embodiments of the disclosed invention, active cooling can be used to access thermal measurement temperatures below ambient via cryogenic levels. By using the disclosed apparatus and method, thermal properties at very narrow temperature intervals can be measured directly.

The structural design of the heater assemblies 12 used in this invention makes them naturally amenable for use at the miniature, microscopic and nano-scopic scales. The heaters are suspended on long self-supported beams 18 such that thermal flux away from the heaters is limited to conduction alone. This heat flux to the surrounding environment is constant throughout the thermal conductivity measurement. That means the thermal flux to the stage 72 is the same in the open condition, with no specimen in place, and in the bridged heater condition, where a test specimen is in contact with both of the heater elements 12a and 12b, simultaneously. Another unique feature of the invention apparatus is the ability to measure thermal conductivity with the specimen under quantitative tensile or compressive loading conditions. Since the gap length 82 between the heater assemblies 12 may be adjusted with the actuator 74 (with the corresponding force being determined by the load cell 76), accurate conductance measurement of the specimen under load may be accomplished.

The present invention may be configured to directly measure the amount of radiant heat loss during elevated temperature measurements. Under low temperature measurement conditions, the change in bridged power requirements to maintain the set temperatures is equal and opposite for the hot and cold heater assemblies (again, the hot and cold nomenclature may be arbitrary assigned to relatively warmer, and cooler heater assemblies 12a or 12b). When radiation heat losses occur, the power increase in the hot side heater becomes larger than the power reduction in the cold side heater. Then, hot side power input provides energy to maintain the heater platen 16 at temperature (including radiant loss of the platen 16 itself), energy that is lost through heat conduction along the test specimen and energy that is lost through radiation heat loss from the sample. However, the radiation loss may be minimized by keeping a low temperature difference between the two heaters.

Using the disclosed apparatus and method, thermal conductivity measurements can be made at temperatures well below room temperature by placing the two heater assemblies 12 on a cooled substrate, essentially reducing the local ambient or bath temperature. This can enable thermal conductivity measurement at cryogenic temperatures approaching 10° Kelvin or below.

Fixed heater platens 16, such as those employed in prior art single-heater embodiments. Then, a balance measurement can be made using a single adjusted heater assembly in the open and bridged states.

While the disclosed invention focuses on one particular structure for implementation of the heater assemblies 12, other forms of heater assemblies may yield acceptable results if sufficiently high resolution in power input can be obtained.

The disclosed methodology can be applied to larger test specimens, even macroscopic testing, so long as one dimensional convective heat flow can be maintained within the sample being measured. This condition requires no convective losses or secondary conduction heat losses, for example to insulating materials.

Other substrate 32 material, dielectric layer 30 or conducting metal layer 34 can be utilized in the fabrication of heater assemblies 12. For example, a replacement substrate 32 material, such as silicon dioxide, with improved mechanical qualities at high temperature may be used. An alternate dielectric layer 30, for example Alumina by plasma enhanced chemical vapor deposition, could be used.

While all the thermal conductivity measurements could be made within an SEM or FIB vacuum chamber, measurements can also be carried out by placing the test rig 70 into a general purpose vacuum chamber equipped provisions capable of accommodating the sealed passage of electrical conductors. However, use of a general purpose vacuum environment necessitates specimen loading via other means such as an optical microscope and external micromanipulation system.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. An apparatus for thermal conductance measurement, the apparatus comprising:
   a first heater assembly having a beam, a platen disposed at an end of the beam, and a first heating element and a Resistance Temperature Device (RTD) disposed on the platen;
   a second heater assembly having a second beam, a second platen disposed at an end of the second beam, and a second heating element and a second Resistance Temperature Device (RTD) disposed on the platen;
   a test rig, wherein the first heater assembly and second heater assembly are mated to the test rig as two independently positionable subassemblies and separated by an adjustable gap; and
   wherein the first heater assembly and the second heater assembly are configured to operably couple to a specimen spanning the gap, and wherein the specimen maintains thermal contact with the first heater assembly and the second heater assembly during a measurement of thermal conductivity.

2. The apparatus of claim 1, further including a power supply electrically coupled to the first heating element or the second heating element, a Source Measuring Unit (SMU) electrically coupled to the first RTD or the second RTD, and a controller electrically coupled to the power supply and the SMU, wherein the controller is configured to maintain the heating element at a desired temperature in response to signals received from the SMU.

3. The apparatus of claim 1, further including a stage disposed between the first heater assembly and the test rig and configured to adjustably orient either the first heater assembly, the second heater assembly, or both of the first and second heater assemblies in three dimensional space; and
   an actuator and load cell disposed between either the second heater assembly and the test rig or between the first heater assembly and the stage, and wherein the actuator and the load cell are configured to cooperatively apply and measure a compressive or tensile force applied to the specimen.

4. A heater assembly, the heater assembly comprising:
   a substrate;
   a beam extending from a portion of the substrate;
   a platen disposed at an end of the beam;
   a heating element and a Resistance Temperature Device (RTD) disposed on the platen;
   pads forming a plurality of electrically conductive regions on the substrate, and
   a plurality of conducting wires electrically mating the pads to the RTD and to the heating element.

5. The heater assembly of claim 4, wherein the beam is a skeletonized structure imparted through the thickness of the substrate, and wherein the beam resists thermal conductance between the platen and the heater assembly.

6. A method for testing the thermal conductance of a specimen in a system having a first platen and a second platen, wherein the first platen includes a first heating element and a first Resistance Temperature Device (RTD), and wherein the second platen includes a second heating element and a second Resistance Temperature Device (RTD), the method including:
   evacuating the air proximate the first heating element and the second heating element;
   using the first and second RTD to obtain temperature data;
   applying a first and second power level to maintain a desired first and second baseline set temperature in each of the first heating element and the second heating element, respectively, while no sample is in place;
   recording the first and second power level required to maintain the desired first and second baseline set temperature in each of the first heating element and the second heating element, respectively;
   adjusting a gap having a distance between the first platen and the second platen based on the specimen dimensions;
   placing the specimen across the gap separating the first platen and the second platen and establishing thermal contact between the specimen and each of the first platen and the second platen;
   applying a third and fourth power level to maintain the desired first and second baseline set temperature in each of the first heating element and the second heating element, respectively, while the specimen is spanning the gap between the first platen and the second platen; and
   recording a difference between-the first power level and the third power level and, between the second power level and the fourth power level, required to maintain the first and second baseline set temperatures.

7. The method of claim 6, further including an actuator and a load cell configured to apply and measure a force applied to the specimen; and
   using the load cell and actuator to apply a desired force to the specimen while the specimen is being tested for thermal conductance.

8. The method of claim 6, further comprising calculating a thermal conductivity of the specimen by using a one-dimensional Fourier's conduction formulation according to $\kappa = -q\,(\Delta x/\Delta T)$, where q is the normalized heat flux and $\kappa$ the thermal conductivity; and
   wherein the power is the difference between-the first power level and the third power level and, between the second power level and the fourth power level, required to maintain the first and second baseline set temperatures.

* * * * *